United States Patent [19]

Higo et al.

[11] 4,237,313

[45] Dec. 2, 1980

[54] RACEMIZATION OF OPTICALLY ACTIVE α-SUBSTITUTED-α-PHENYLACETIC ACID DERIVATIVES

[75] Inventors: Akio Higo, Osaka; Yukio Suzuki, Toyonaka, both of Japan

[73] Assignee: Sumitomo Chemical Company, Limited, Osaka, Japan

[21] Appl. No.: 34,696

[22] Filed: Apr. 30, 1979

[30] Foreign Application Priority Data

Apr. 28, 1978 [JP] Japan .................................. 53/52101

[51] Int. Cl.² ............................................. C07B 20/00
[52] U.S. Cl. ............................ 562/401; 260/340.5 R; 260/340.3
[58] Field of Search ................ 562/401, 465, 496, 491; 260/346.22, 340.5 R, 340.3

[56] References Cited

U.S. PATENT DOCUMENTS

| | | | |
|---|---|---|---|
| 3,213,106 | 10/1965 | Sasaji et al. ........................... | 562/401 |
| 3,737,454 | 6/1973 | Chibata et al. ........................ | 562/401 |

FOREIGN PATENT DOCUMENTS

| | | | |
|---|---|---|---|
| 366842 | 3/1963 | Switzerland ............................. | 562/401 |
| 950550 | 2/1964 | United Kingdom ..................... | 562/401 |

*Primary Examiner*—Natalie Trousof
*Assistant Examiner*—Vera C. Clarke
*Attorney, Agent, or Firm*—Sughrue, Rothwell, Mion, Zinn and Macpeak

[57] ABSTRACT

A process for racemization of optically active phenylacetic acid derivatives, which comprises heating an optically active phenylacetic acid derivative of the formula (I):

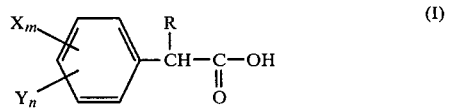

wherein X and Y, which may be the same or different, each represents a hydrogen atom, a halogen atom, a lower alkyl group, a lower alkoxy group, a halogen-substituted lower alkyl group or a halogen-substituted lower alkoxy group, or X and Y may jointly form an alkylenedioxy group; m and n, which may be the same or different, each represents an integer of 1 to 5, and the sum of m and n does not exceed 5; and R represents an isopropyl group or a cyclopropyl group, to a temperature of at least 150° C. in the presence or absence of an inert solvent.

8 Claims, No Drawings

RACEMIZATION OF OPTICALLY ACTIVE α-SUBSTITUTED-α-PHENYLACETIC ACID DERIVATIVES

BACKGROUND OF THE INVENTION

1. Field of the Invention

This invention relates to a process for the racemization of optically active phenylacetic acid derivatives of the following general formula (I). More specifically, the invention relates to a process for the racemization of optically active α-cyclopropylphenylacetic acid derivatives or α-isopropylphenylacetic acid derivatives.

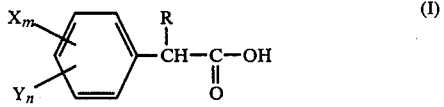

wherein X and Y, which may be the same or different, each represents a hydrogen atom, a lower alkyl group, a lower alkoxy group, a halogen-substituted lower alkyl group or a halogen-substituted lower alkoxy group, or X and Y may jointly form an alkylenedioxy group; m and n, which may be the same or different, each represents an integer of 1 to 5, and the sum of m and n does not exceed 5; and R represents an isopropyl group or a cyclopropyl group.

2. Description of the Prior Art

It is already known that a group of α-substituted phenylacetic esters having a greatly different structure from conventional pyrethroid-type insecticides have a strong insecticidal activity on various noxious insects (Japanese Patent Application (OPI) Nos. 26425/74, 126826/74 and 1315563/77). (The term "OPI" as used herein refers to a "published unexamined Japanese patent application".) Among these, esters of phenylacetic acid derivatives in which the substituent in the α-position is an isopropyl or cyclopropyl group have recently attracted attention because of their superior effect. Particularly, esters of 2-(4-chlorophenyl)-3-methylbutyric acid are excellent in respect of their effect and cost economy.

Various investigations were made about the insecticidal effect of esters of optically active carboxylic acids obtained by the optical resolution of α-substituted phenylacetic acids which are the constituent element of the above-described esters. Out of these investigations, methods for the optical resolution of a series of α-substituted phenylacetic acids emerged (Japanese Patent Application (OPI) Nos. 25544/75 and 106935/75).

However, mere production of effective active isomers by optical resolution cannot generally be said to be an industrial achievement. It is not until a method of effective utilization of the separated and removed enantiomers is discovered that such a technique becomes useful. In view of this, the present inventors made extensive investigations about a method of racemizing optically active carboxylic acids and derivatives thereof with a view to effectively utilizing the separated enantiomers. In particular, as to the esters of 2-(4-chlorophenyl)-3-methylbutyric acid, those of d-isomer are more effective, and the present inventors made extensive investigations about a method of optically resolving such carboxylic acid and a method of racemizing an l-isomer thereof produced as a by-product.

Some reports have been made in the past on the racemization of optically active α-substituted phenylacetic acid derivatives.

For example, A. Horeau et al reported that optically active α-ethylphenylacetic acid chloride was easily racemized in pyridine (0.4 M solution) at room temperature and that the rate of racemization was such that the optical rotation decreased to one-seventh of its initial value in about 3 hours [*Bull Soc. Chim. Fr.*, 117 (1967)]. In the same report, Horeau et al described that optically active α-ethylphenylacetic anhydride was racemized in pyridine at room temperature. The rate of racemization was such that the optical rotation decreased to one-half of the initial value in as long as 20 hours when the concentration of the pyridine solution was 0.1 M, while the racemization completely came to an end in about 8 hours when the concentration was 0.6 M.

H. Collet et al reported that optically active α-ethylphenylacetic acid is racemized by mixing with equimolar proportions of trifluoroacetic acid and trifluoroacetic anhydride [*Tetrahedron*, 28, 5883 (1972)].

Ph. Gold-Aubert reported that optically active N-α-(α-ethylphenylacetyl)urea was racemized to about 73% when heated under reflux for 90 minutes in 0.5 N NaOH in 50% aqueous ethanol [*Helv. Chem. Acta.*, 168, 1513 (1958)].

R. S. Stuart et al examined the rate at which the hydrogen atom in the α-position of phenylacetic acids was exchanged with heavy hydrogen when the sodium salt of the phenylacetic acids was placed in deuterium oxide in the presence of an alkali. Based on this investigation, they reported that the rate of heavy hydrogen exchange was about 1/270 for sodium α-metjhylphenylacetate and about 1/42,000 for sodium α-isopropylphenylacetate based on the rate of heavy hydrogen exchange at 90° C. of the sodium α-methylphenylacetate [*J. Chem. Soc., Chem. Commun.*, 1068 (1969)].

Japanese Patent Application (OPI) No. 5134/78 discloses a process for racemizing an optically active alkali metal 2-(4-chlorophenyl)-3-methylbutyrate by heating in the presence of an alkali, etc. Japanese Patent Application (OPI) No. 3035/79 discloses that optically active 2-(4-chlorophenyl)-3-methylbutyroyl chloride can be very easily racemized by heating.

However, these processes are not directed to the racemization of carboxylic acids themselves, but pertain to the racemization of carboxylic acids in the form of various derivatives such as metal salts or acid chlorides. When the carboxylic acids are used again as a raw material for optical resolution, these derivatives should be converted back to the free acids. For this reason, at least one additional step is required, and extra reaction adjuvants are necessary.

Further investigations under the foregoing background led to the surprising discovery that optically active 2-(4-chlorophenyl)-3-methylbutyric acid can be racemized simply by heating to at least 150° C., preferably to at least 200° C. The present inventors also ascertained that analogous phenylacetic acid derivatives can be racemized under similar conditions. This has finally led to the accomplishment of the present invention.

SUMMARY OF THE INVENTION

An object of the present invention is to provide a process for racemizing the optically active phenylacetic acid derivatives of the general formula (I):

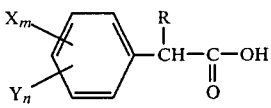

(I)

wherein X and Y, which may be the same or different, each represents a hydrogen atom, a halogen atom, a lower alkyl group, a lower alkoxy group, a halogen-substituted lower alkyl group or a halogen-substituted lower alkoxy group, or X and Y may jointly form an alkylenedioxy group; m and n, which may be the same or different, each represents an integer of 1 to 5, and the sum of m and n does not exceed 5; and R represents an isopropyl group or a cyclopropyl group, which comprises heating the phenylacetic acid derivatives of the general formula (I) to a temperature of at least 150° C. in the presence or absence of an inert solvent.

To the best of the knowledge of the present inventors, this fact of heat racemization of the α-substituted phenylacetic acids themselves has not been described in any literature references.

DETAILED DESCRIPTION OF THE INVENTION

Since the process of this invention enables the carboxylic acid of general formula (I) to be racemized directly without going through its derivative, it is very advantageous commercially from the standpoint of economy and the ease of operation.

In the phenylacetic acid derivatives of general formula (I), the lower alkyl and lower alkoxy groups are preferably those having 1 to 4 carbon atoms, respectively, with a methyl group and a methoxy group being especially preferred. Preferred halogen-substituted lower alkyl groups and halogen-substituted lower alkoxy groups are alkyl and alkoxy groups each having 1 to 4 carbon atoms and each substituted with at least one halogen atom, especially fluorine. When X and Y jointly form an alkylenedioxy group, a 3,4-methylenedioxy group is especially preferred.

In view of cost economy and effect, phenylacetic acid derivatives of the following general formula (II):

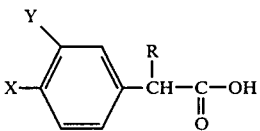

(II)

wherein X, Y and R are the same as defined hereinabove, are preferred among those of the general formula (I). In particular, the esters of 2-(4-chlorophenyl)-3-methylbutyric acid are excellent in economy and effect, and an α-cyano-3-phenoxybenzyl alcohol ester thereof (generally called as "Fenvalerate") is becoming an important insecticide.

In the present invention, racemization proceeds even at below 150° C., but the rate of racemization is slow, thus such is not practical. The racemization proceeds more rapidly as the temperature is high. In view of the heat stability of the carboxylic acid (I), however, the racemization temperature is preferably up to about 400° C. Accordingly, the racemization temperature employed in this invention is usually from 150° C. to 400° C., preferably from 200° C. to 350° C.

Usually, the process of this invention is carried out under atmospheric pressure, but may be carried out under elevated or reduced pressures. It can be performed either in the liquid phase or in the gaseous phase.

A solvent is not particularly required in the performance of the process of this invention. If desired, however, an inert solvent may be used. Suitable inert solvents which can be used are those having a boiling point of 150° C. or higher, preferably 200° C. or higher, but the present invention is not limited thereto. Specific examples of these inert solvents include hydrocarbons such as diethylbenzene, pseudocumene, mesitylene, disphenyl, tetralin, decalin, etc., ethers such as diphenyl ether, m-tolylphenyl ether, etc., halogenated hydrocarbons such as pentachlorobenzene, and sulfuric acid. Desirably, the reaction is carried out in an atmosphere of an inert gas such as nitrogen or argon, but such is not essential.

It is possible to convert an optically active carboxylic acid, which is formed as a by-product during the optical resolution of an α-substituted phenylacetic acid derivative, into a racemic carboxylic acid by the process of this invention described hereinabove, and to subject the racemic carboxylic acid again to optical resolution either directly or after subjecting to a purifying step such as recrystallization. This procedure makes it possible to effectively utilize the separated and removed optically active carboxylic acid by a very simple method.

The degree of racemization can be known by measuring the optical rotation of the phenylacetic acid derivative; or by converting the carboxylic acid to an acid chloride using thionyl chloride or the like, reacting the acid chloride with an optically active reagent such as l-menthol or the like, and measuring the ratio of diastereomers by such a means as gas chromatography.

The following Examples illustrate the present invention more specifically, but it should be understood that the invention is not limited to these Examples.

EXAMPLE 1

50.0 g of l-isomer rich 2-(4-chlorophenyl)-3-methylbutyric acid ($[\alpha]_D^{23°\,C.} = -35.4°$ (C=6.0, in chloroform)) was charged into a 200 ml flask, and stirred at 215° C. for 12 hours in a nitrogen atmosphere. The thus obtained 2-(4-chlorophenyl)-3-methylbutyric acid was found to have an optical rotation, $[\alpha]_D^{23°\,C.}$, of $-1.2°$ (C=6, in chloroform), and to be almost completely racemized.

EXAMPLE 2

A mixture of 59.52 g of l-isomer rich 2-(4-chlorophenyl)-3-methylbutyric acid used in Example 1 and 365.2 g of 64% sulfuric acid was charged into a 500 ml flask, and stirred under reflux for 6 hours (the inside temperature: 150° C.). After cooling, toluene was added thereto, and the carboxylic acid was recovered. The product thus obtained was found to have an optical rotation, $[\alpha]_D^{23°\,C.}$, of $-30.71°$ (C=6.0, in chloroform), and the degree of racemization was about 13%.

EXAMPLE 3

5 g of l-isomer rich 2-(4-chlorophenyl)-3-methylbutyric acid used in Example 1 was charged into a 20 ml flask, and heated at 180° C. for 12 hours in a nitrogen atmosphere. After heat-treating, the contents of the flask was taken out. The optical rotation, $[\alpha]_D^{23°\,C.}$, of the product was $-22.7°$ (C=6.0, in chloroform), and the degree of racemization was 36%.

EXAMPLES 4 TO 8

The same procedure as that in Example 3 was repeated under the various conditions shown in Table 1 below. The results thus obtained are shown in Table 1.

TABLE 1

| Example No. | Treating Conditions Temperature (°C.) | Time (min.) | Optical Rotation of the Contents of the Flask after the Treatment $[\alpha]_D^{23\,°C.}$; C = 6.0; in Chloroform | Degree of Racemization (%) |
|---|---|---|---|---|
| 4 | 200 | 600 | −8.19° | 77 |
| 5 | 220 | 360 | −1.13° | 97 |
| 6 | 250 | 60 | −1.07° | 97 |
| 7 | 280 | 10 | −0.79° | 98 |
| 8 | 300 | 3 | −0.24° | 99 |

EXAMPLE 9

A mixture of 6 g of l-isomer rich 2-(4-chlorophenyl)-3-methylbutyric acid used in Example 1 and 30 g of m-tolylphenyl ether was charged into a 100 ml flask, and stirred for 1 hours under reflux in a nitrogen atmosphere (the inside temperature: 270° C.). After cooling, toluene was added thereto to dilute the reaction mixture. The diluted mixture was extracted with a 5% aqueous solution of sodium hydroxide to separate the carboxylic acid, and acid precipitation with a 10% aqueous solution of HCl was performed. Thereafter, toluene was added to the system, and the carboxylic acid was recovered. The optical rotation of the carboxylic acid was $[\alpha]_D^{23\,°C.} = -0.32°$ (C=6.0, in chloroform), and the degree of racemization was 99%.

EXAMPLE 10

A mixture of 6 g of l-isomer rich 2-(4-chlorophenyl)-3-methylbutyric acid used in Example 1 and 30 g diphenyl ether was charged into a 100 ml flask, and stirred for 2 hours under reflux in a nitrogen atmosphere (the inside temperature: 258° C.). After cooling, the same operation as that in Example 9 was performed, and the optical rotation of the product was measured. It was $[\alpha]_D^{23\,°C.} = -0.16°$ (C=6.0, in chloroform). The degree of racemization was 100%.

EXAMPLE 11

A mixture of 6 g of l-isomer rich 2-(4-chlorophenyl)-3-methylbutyric acid used in Example 1 and 30 g of diphenyl was charged into a 100 ml flask, and stirred for 2 hours under reflux in a nitrogen atmosphere (the inside temperature: 256° C.). After cooling, the same operation as that in Example 9 was performed. The optical rotation of the product was found to be $[\alpha]_D^{23\,°C.} = -0.19°$ (C=6.0, in chloroform). The degree of racemization was 99%.

EXAMPLES 12 TO 20

One gram of each of the various optially active phenylacetic acid derivatives shown in Table 2 below was charged into a test tube, and heated in a nitrogen atmosphere under the conditions shown in Table 2 to racemize the phenylacetic acid derivative. In all Examples, the degree of racemization was high. The results thus obtained are shown in Table 2.

TABLE 2

Phenylacetic Acid Derivative

| Example No. | X | Y | R | Heating Temperature (°C.) | Heating Time (hours) | Optical Rotation Before Racemization in Chloroform | Optical Rotation After Racemization in Chloroform |
|---|---|---|---|---|---|---|---|
| 12 | H | H | −CH(CH₃)₂ | 220 | 10 | $[\alpha]_D^{24}$ −52.3° (C = 2.1) | $[\alpha]_D^{24}$ −1.2° (C = 3.0) |
| 13 | 4-CH₃ | " | " | 230 | 8 | $[\alpha]_D^{25}$ −45.9° (C = 1.7) | $[\alpha]_D^{25}$ −2.1° (C = 2.8) |
| 14 | 4-F | " | " | 230 | 8 | $[\alpha]_D^{24}$ −32.3° (C = 1.6) | $[\alpha]_D^{24}$ −0.1° (C = 1.9) |
| 15 | 2-Cl | " | " | 230 | 8 | $[\alpha]_D^{22}$ +42.0° (C = 2.0) | $[\alpha]^{24}$ +1.5° (C = 2.0) |
| 16 | 3-Cl | " | " | 300 | 5 (minutes) | $[\alpha]_D^{24}$ +33.5° (C = 3.2) | $[\alpha]_D^{24}$ +0.3° (C = 3.0) |
| 17 | 4-Cl | " | −CH(CH₂)₂ (cyclopropyl) | 230 | 8 | $[\alpha]_D^{24.5}$ −32.6° (C = 2.0) | $[\alpha]_D^{24}$ −0.4° (C = 3.1) |
| 18 | 4-Br | " | −CH(CH₃)₂ | 230 | 8 | $[\alpha]_D^{23.5}$ −28.7° (C = 2.3) | $[\alpha]_D^{24}$ −0.2° (C = 2.2) |
| 19 | 4-CH₃O— | " | " | 200 | 20 | $[\alpha]_D^{24}$ −35.0° (C = 2.3) | $[\alpha]_D^{24}$ −0.7° (C = 2.5) |
| 20 | 3,4-Methylenedioxy | " | " | 230 | 8 | $[\alpha]_D^{23}$ −31.9° (C = 1.7) | $[\alpha]_D^{23}$ −0.7° (C = 2.1) |

While the invention has been described in detail and with reference to specific embodiments thereof, it will be apparent to one skilled in the art that various changes and modifications can be made therein without departing from the spirit and scope thereof.

What is claimed is:

1. A process for racemization of optically active phenylacetic acid derivatives, which comprises heating an optically active phenylacetic acid derivative of the general formula (I):

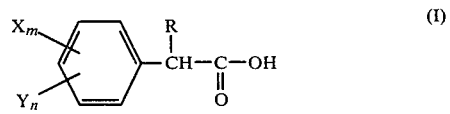

wherein X and Y, which may be the same or different, each represents a hydrogen atom, a halogen atom, a lower alkyl group, a lower alkoxy group, a halogen-substituted lower alkyl group or a halogen-substituted lower alkoxy group, or X and Y may jointly form an alkylenedioxy group; m and n, which may be the same or different, each represents an integer of 1 to 5, and the sum of m and n does not exceed 5; and R represents an isopropyl group or a cyclopropyl group, to a temperature of at least 150° C. in the presence or absence of an inert solvent.

2. The process of claim 1, wherein the optically active phenylacetic acid derivative is expressed by the general formula (II):

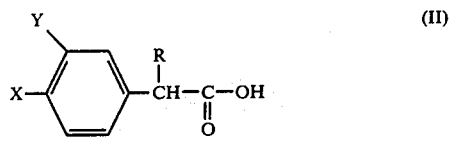

wherein X, Y and R are the same as defined in claim 1.

3. The process of claim 1, wherein the substituent R is an isopropyl group.

4. The process of claim 2, wherein the substituent R is an isopropyl group.

5. The process of claim 1, wherein the optically active phenylacetic acid derivative is 2-(4-chlorophenyl)-3-methylbutyric acid.

6. The process of claim 1, wherein the optically active phenylacetic acid derivative is 2-cyclopropyl-2-(4-chlorophenyl)acetic acid.

7. The process of any one of claims 1 to 6, wherein the heating temperature is from 200° C. to 350° C.

8. The process of any one of claims 1 to 7, wherein the heating is carried out in the absence of a solvent.

* * * * *